US008724868B2

(12) United States Patent
Wang et al.

(10) Patent No.: US 8,724,868 B2
(45) Date of Patent: *May 13, 2014

(54) SYSTEM AND METHOD FOR DISPLAY OF PANORAMIC CAPSULE IMAGES

(75) Inventors: Kang-Huai Wang, Saratoga, CA (US); Gordon C Wilson, San Francisco, CA (US)

(73) Assignee: Capso Vision, Inc., Saratoga, CA (US)

( * ) Notice: Subject to any disclaimer, the term of this patent is extended or adjusted under 35 U.S.C. 154(b) by 356 days.

This patent is subject to a terminal disclaimer.

(21) Appl. No.: 13/329,212

(22) Filed: Dec. 16, 2011

(65) Prior Publication Data

US 2012/0086771 A1 Apr. 12, 2012

Related U.S. Application Data

(63) Continuation-in-part of application No. 12/577,626, filed on Oct. 12, 2009.

(51) Int. Cl.
*G06K 9/00* (2006.01)

(52) U.S. Cl.
USPC .......................................... 382/128; 382/284

(58) Field of Classification Search
None
See application file for complete search history.

(56) References Cited

U.S. PATENT DOCUMENTS

| 5,604,531 | A | * | 2/1997 | Iddan et al. ..................... 348/76 |
| 6,918,872 | B2 | * | 7/2005 | Yokoi et al. .................. 600/129 |
| 6,939,292 | B2 | * | 9/2005 | Mizuno ......................... 600/118 |
| 6,944,316 | B2 | * | 9/2005 | Glukhovsky et al. ......... 382/107 |
| 6,951,536 | B2 | * | 10/2005 | Yokoi et al. .................. 600/128 |
| 7,343,036 | B2 | * | 3/2008 | Kleen et al. .................. 382/154 |
| 7,813,590 | B2 | * | 10/2010 | Horn et al. .................... 382/284 |
| 7,817,354 | B2 | | 10/2010 | Wilson |
| 7,983,458 | B2 | | 7/2011 | Wang et al. |
| 2003/0171648 | A1 | * | 9/2003 | Yokoi et al. .................. 600/109 |
| 2003/0171649 | A1 | * | 9/2003 | Yokoi et al. .................. 600/109 |
| 2004/0264754 | A1 | * | 12/2004 | Kleen et al. .................. 382/128 |
| 2006/0285732 | A1 | * | 12/2006 | Horn et al. .................... 382/128 |
| 2007/0221233 | A1 | * | 9/2007 | Kawano et al. ............... 128/899 |
| 2008/0123954 | A1 | * | 5/2008 | Ekstrand et al. ............. 382/173 |
| 2008/0143822 | A1 | | 6/2008 | Wang et al. |
| 2009/0074265 | A1 | | 3/2009 | Huang |

* cited by examiner

*Primary Examiner* — John Strege
(74) *Attorney, Agent, or Firm* — Blairtech Solution LLC

(57) ABSTRACT

Systems and methods are provided for displaying images captured from a panoramic capsule camera system. In one embodiment according to the invention, multiple sub-image sets are generated using a sub-image set window on the panoramic image by cyclically shifting the panoramic image. The multiple sub-image sets are then displayed in multiple display windows. In another embodiment according to the invention, the sub-image set in every other display window is flipped horizontally, vertically or both horizontally and vertically.

8 Claims, 13 Drawing Sheets

SYSTEM AND METHOD FOR DISPLAY OF PANORAMIC CAPSULE IMAGES

CROSS REFERENCE TO RELATED APPLICATIONS

The present invention is a continuation-in-part of and claims priority to U.S. Non-Provisional patent application Ser. No. 12/577,626, filed on Oct. 12, 2009, entitled "System and Method for Display of Panoramic Capsule Images". The U.S. Non-Provisional patent applications is hereby incorporated by reference in its entirety.

FIELD OF THE INVENTION

The present invention relates to diagnostic imaging inside the human body. In particular, the present invention relates to displaying images captured by a panoramic camera system.

BACKGROUND

Devices for imaging body cavities or passages in vivo are known in the art and include endoscopes and autonomous encapsulated cameras. Endoscopes are flexible or rigid tubes that pass into the body through an orifice or surgical opening, typically into the esophagus via the mouth or into the colon via the rectum. An image is formed at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they do have a number of limitations, present risks to the patient, are invasive and uncomfortable for the patient, and their cost restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscope. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An autonomous capsule camera system with on-board data storage was disclosed in the U.S. patent application Ser. No. 11/533,304, entitled "In Vivo Autonomous Camera with On-Board Data Storage or Digital Wireless Transmission in Regulatory Approved Band," filed on Sep. 19, 2006. This application describes a capsule system using on-board storage such as semiconductor nonvolatile archival memory to store captured images. After the capsule passes from the body, it is retrieved. Capsule housing is opened and the images stored are transferred to a computer workstation for storage and analysis.

The above mentioned capsule cameras use forward looking view where the camera looks toward the longitude direction from one end of the capsule camera. It is well known that there are sacculations that are difficult to see from a capsule that only sees in a forward looking orientation. For example, ridges exist on the walls of the small and large intestine and also other organs. These ridges extend somewhat perpendicular to the walls of the organ and are difficult to see behind. A side or reverse angle is required in order to view the tissue surface properly. Conventional devices are not able to see such surfaces, since their FOV is substantially forward looking. It is important for a physician to see all areas of these organs, as polyps or other irregularities need to be thoroughly observed for an accurate diagnosis. Since conventional capsules are unable to see the hidden areas around the ridges, irregularities may be missed, and critical diagnoses of serious medical conditions may be flawed.

A camera configured to capture a panoramic image of an environment surrounding the camera is disclosed in U.S. patent application Ser. No. 11/642,275, entitled "In vivo sensor with panoramic camera" and filed on Dec. 19, 2006. The panoramic camera is configured with a longitudinal field of view (FOV) defined by a range of view angles relative to a longitudinal axis of the capsule and a latitudinal field of view defined by a panoramic range of azimuth angles about the longitudinal axis such that the camera can capture a panoramic image covering substantially a 360 deg latitudinal FOV.

Conceptually, multiple individual cameras configured to cover may be used to cover completely or substantially a 360 deg latitudinal FOV. However, such panoramic capsule system may be expensive since multiple image sensors and associated electronics may be required. A cost-effective panoramic capsule system is disclosed in U.S. patent application Ser. No. 11/624,209, entitled "Panoramic Imaging System", filed on Jan. 17, 2007. The panoramic capsule system uses an optical system configured to combine several fields-of-view to cover a 360° view. Furthermore, the combined fields-of-view is projected onto a single sensor to save cost. Therefore, this single sensor capsule system functions effectively as multiple cameras at a lower cost.

For capsule systems with either digital wireless transmission or on-board storage, the captured images will be played back for analysis and examination. During playback, the diagnostician wishes to find polyps or other points of interest as quickly and efficiently as possible. The playback is at a controllable frame rate and may be increased to reduce viewing time. However, if the frame rate is increased too much, the gyrations of the field of view (FOV) will make the video stream difficult to follow. At whatever frame rate, image gyration demands more cognitive effort on the diagnostician's part to follow, resulting in viewer fatigue and increased chance of missing important information in the video.

For images generated by a panoramic camera, the image usually has a wide aspect ratio (the picture width to picture height ratio). In some applications, the constituent images captured may have to be stitched to form a proper panoramic image. For example, in U.S. patent application Ser. No. 11/856,098, entitled "Imaging review and navigation workstation system", filed on Sep. 17, 2007, a method to stitch multiple constituent images corresponding to a scene of a surface of a tube is disclosed. Each of the constituent images captured by a capsule camera is a distorted image of a projection of each point in the scene captured by a constituent image onto the tubular surface, where lines of projection are toward a center of perspective associated with the constituent image. The center of perspective for each constituent image is within the tubular surface. For panoramic camera systems having either multiple cameras or using an optical system to combine multiple fields-of-view, the aspect ratio of the composite image becomes extreme wide. In one example, the panoramic image may be stitched from 4 fields-of-view where each individual image may have an aspect ratio of 2:1. The resulting image will have an aspect ratio of 8:1. Based on general viewing experience, when viewing an image with such a wide aspect ratio, the eyes often tend to focus from one place to the other instead of looking at the picture as a whole. This may increase the likelihood of failing to identify anomaly. It is desirable to provide a display method and system suited for viewing panoramic images, particularly providing a diagnostician a reliable and comfortable viewing environment. Furthermore, the time spent by a diagnostician to review the image sequence represents a sizable cost of the medical procedure of imaging body. A method and system that can reduce the viewing time without compromising diagnostician's reliability.

SUMMARY

The present invention provides an effective method and system for viewing an image sequence generated from a panoramic camera system. In one embodiment, a method for displaying video of panorama images from a capsule camera system is disclosed which comprises accepting a panorama image captured with the capsule camera system; generating multiple sub-image sets using a sub-image set window on the panoramic image by cyclically shifting the panoramic image; and displaying said multiple sub-image sets in multiple display windows, wherein each of said multiple display windows is used to display one of said multiple sub-image sets. The sub-image set in every other display window is flipped horizontally, vertically or both horizontally and vertically In another embodiment of the invention, the method comprises accepting a panorama image captured with the capsule camera system, wherein the panorama image consists of multiple sub-images corresponding to scenes around latitudinal field of view; generating multiple sub-image sets by cyclically shifting the panoramic image; and displaying said multiple sub-image sets in multiple display windows, wherein each of said multiple display windows is used to display one of said multiple sub-image sets.

DETAILED DESCRIPTION OF THE INVENTION

Figure 1:
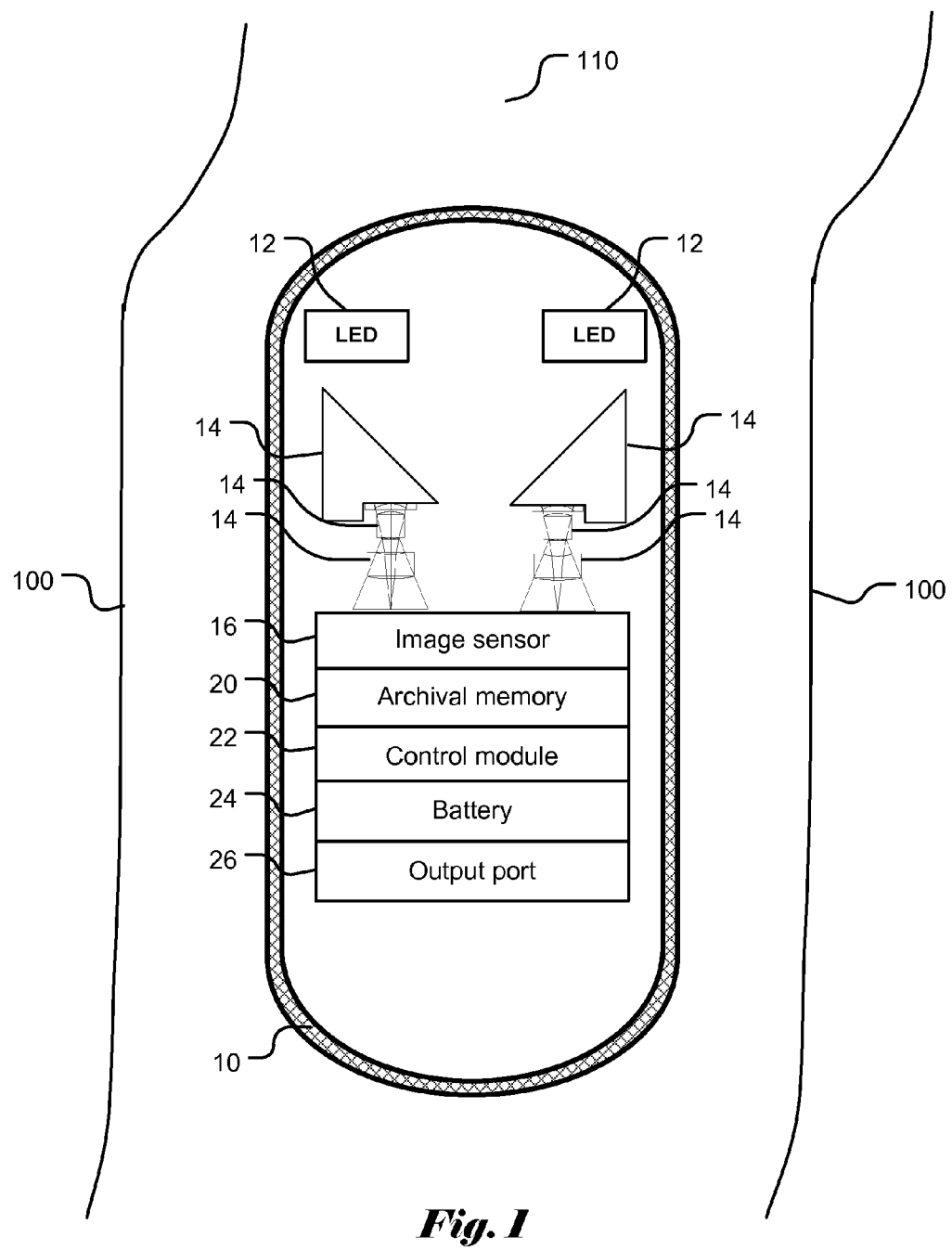
FIG. 1 shows schematically a panoramic capsule camera system in the GI tract, where archival memory is used to store panoramic images to be analyzed and/or examined.

It will be readily understood that the components of the present invention, as generally described and illustrated in the figures herein, may be arranged and designed in a wide variety of different configurations. Thus, the following more detailed description of the embodiments of the systems and methods of the present invention, as represented in the figures, is not intended to limit the scope of the invention, as claimed, but is merely representative of selected embodiments of the invention.

Reference throughout this specification to "one embodiment," "an embodiment," or similar language means that a particular feature, structure, or characteristic described in connection with the embodiment may be included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. One skilled in the relevant art will recognize, however, that the invention can be practiced without one or more of the specific details, or with other methods, components, etc. In other instances, well-known structures, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of apparatus and methods that are consistent with the invention as claimed herein.

Most cameras are designed to create an image with a perspective that is a projection onto a plane. Camera distortion represents a deviation from this ideal planar perspective and may be compensated with post processing using a model of the camera obtained by camera calibration. With in vivo imaging using a wide-angle or panoramic camera, the distortion of the camera is large and the object imaged is highly non-planar. In the case of a panoramic camera, a plane-projected perspective is not possible.

The small bowel and colon are essentially tubes and the capsule camera is a cylinder within the tube. The capsule is on average aligned to the longitudinal axis of the organ. The colon is less tubular than the small bowel, having sacculations. Also, the colon is larger so the orientation of the capsule is less well maintained. However, to first order, the object imaged can be modeled as a cylinder in either case. This is a much better approximation than modeling it as a plane. The cylindrical approximation makes particular sense for a capsule with side facing cameras, such as a single panoramic objective, a single objective that rotates about the longitudinal axis of the capsule, or a plurality of objectives facing in different directions that together capture a panorama. A side-facing camera looks at a small local section which is better approximated as a cylinder than a longer section.

FIG. 1 shows a swallowable capsule system 110 inside body lumen 100, in accordance with one embodiment of the present invention. Lumen 100 may be, for example, the colon, small intestines, the esophagus, or the stomach. Capsule system 110 is entirely autonomous while inside the body, with all of its elements encapsulated in a capsule housing 10 that provides a moisture barrier, protecting the internal components from bodily fluids. Capsule housing 10 is transparent, so as to allow light from the light-emitting diodes (LEDs) of illuminating system 12 to pass through the wall of capsule housing 10 to the lumen 100 walls, and to allow the scattered light from the lumen 100 walls to be collected and imaged within the capsule. Capsule housing 10 also protects lumen 100 from direct contact with the foreign material inside capsule housing 10. Capsule housing 10 is provided a shape that enables it to be swallowed easily and later to pass through of the GI tract. Generally, capsule housing 10 is sterile, made of non-toxic material, and is sufficiently smooth to minimize the chance of lodging within the lumen.

As shown in FIG. 1, capsule system 110 includes illuminating system 12 and a camera that includes optical system 14 and image sensor 16. A semiconductor nonvolatile archival memory 20 may be provided to allow the images to be retrieved at a docking station outside the body, after the capsule is recovered. System 110 includes battery power supply 24 and an output port 26. Capsule system 110 may be propelled through the GI tract by peristalsis.

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. One function of control module 22 is to control the LEDs during image capture operation.

Figure 2:
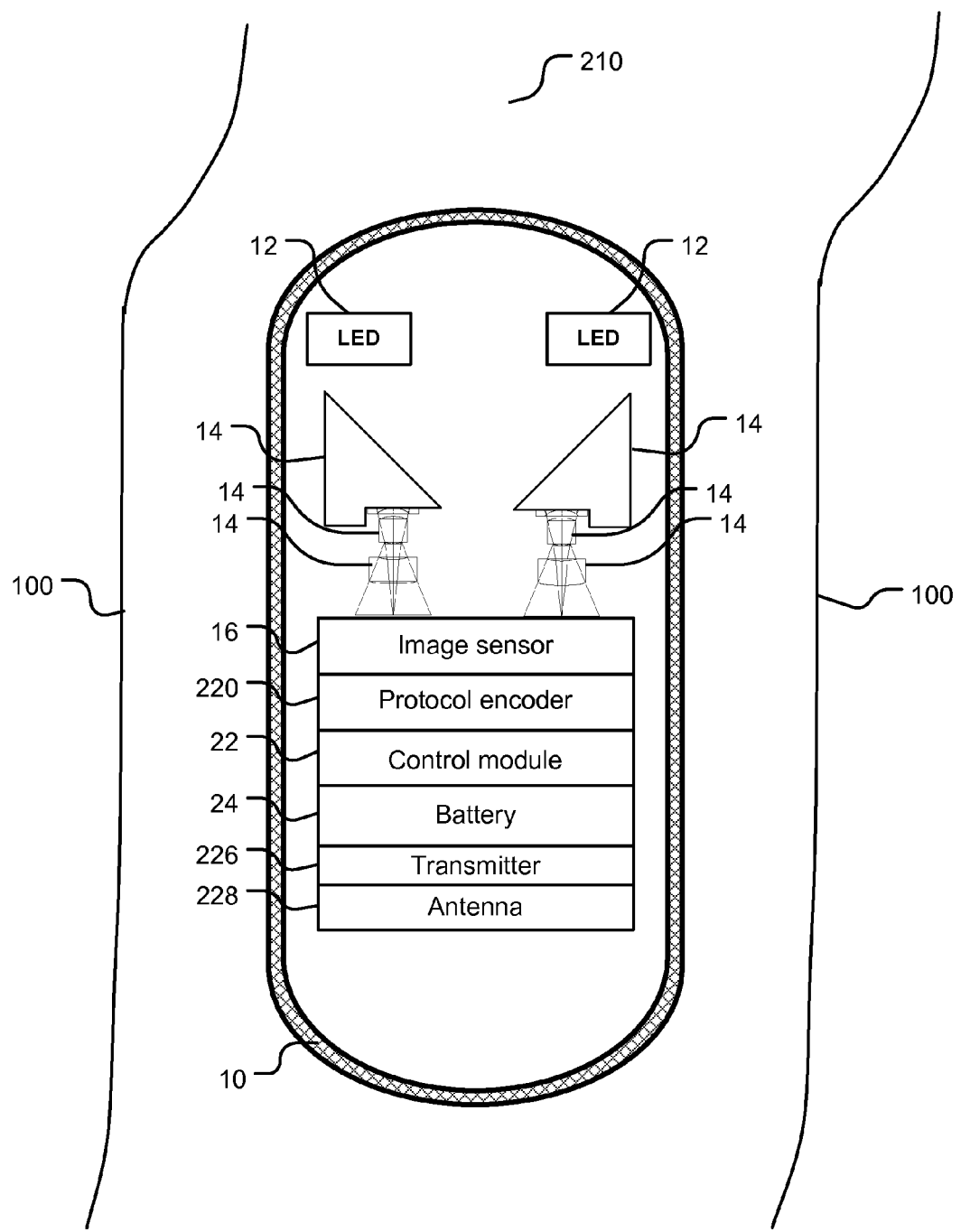
FIG. 2 shows schematically a panoramic capsule camera system in the GI tract, where wireless transmission is used to send panoramic images to a base station for further analysis and/or examination.

FIG. 2 shows an alternative swallowable capsule system 210. Capsule system 210 may be constructed substantially the same as capsule system 110 of FIG. 1, except that archival memory system 20 and output port 26 are no longer required. Capsule system 210 also includes communication protocol encoder 220, transmitter 226 and antenna 228 that are used in the wireless transmission to transmit captured images to a receiving device attached or carried by the person being administered with a capsule system 210. The elements of capsule 110 and capsule 210 that are substantially the same are therefore provided the same reference numerals. Their constructions and functions are therefore not described here repeatedly. Communication protocol encoder 220 may be implemented in software that runs on a DSP or a CPU, in hardware, or a combination of software and hardware. Transmitter 226 and antenna system 228 are used for transmitting the captured digital image.

The panoramic camera system shown in FIG. 1 and FIG. 2 is based on a system using a pyramidal reflective element having multiple reflective side facets facing in different directions. Each of the reflective side facets is associated with a component image in its respective direction. The panoramic camera system combines the component images to form a composite image. There are also other types of panoramic camera systems. For example, in U.S. patent application Ser. No. 11/642,275, entitled "In vivo sensor with panoramic camera" and filed on Dec. 19, 2006, a panoramic camera system using a panoramic annular lens is described. The panoramic annular lens is configured to enable images to be captured by the panoramic camera radially about the longitudinal axis and onto the single image plane. The panoramic images captured by the system having panoramic annular lens reflective side facets represent continuous field of view up to 360°. On the other hand, the panoramic images captured by the system having a reflective element with multiple reflective side facets may represent multiple contiguous fields-of-view.

Though the panoramic images may correspond to a 360° view of the lumen, a practical and convenient way to view the panoramic images is on a display screen which is essentially flat. Therefore the panoramic image has to be properly placed on the flat screen for viewing. For example, the panoramic image captured by the panoramic camera system with a 4-sided reflective element has 4 component images. Each component image corresponds to an image captured in a perspective direction and each component image may be slightly overlapped with its two neighboring component images. The 4 component images are connected in a circular fashion. Images captured by a panoramic camera having a panoramic annular lens will provide continuous fields-of-view and have no boarder lines within the image.

Figure 3:
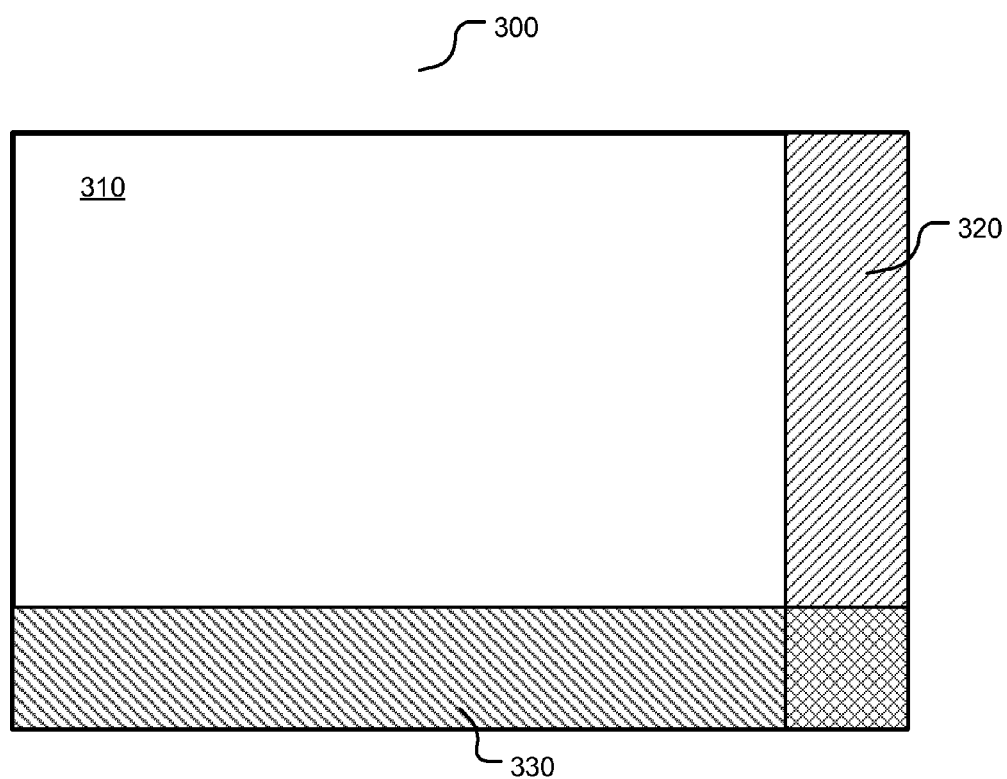
FIG. 3 shows a video screen divided into a display window for displaying video and information bars for displaying information associated with the underlying capsule images.

FIG. 3 shows a display screen 300 for displaying the sequence of panoramic images. The display screen 300 may reserve some screen areas 320 and 330 for displaying other information such as patient information associated with the underlying image sequence and/or the location information, if available, of the current image being shown. The area 310 is designated as the display window for showing the sequence of capsule images.

Figure 4A:
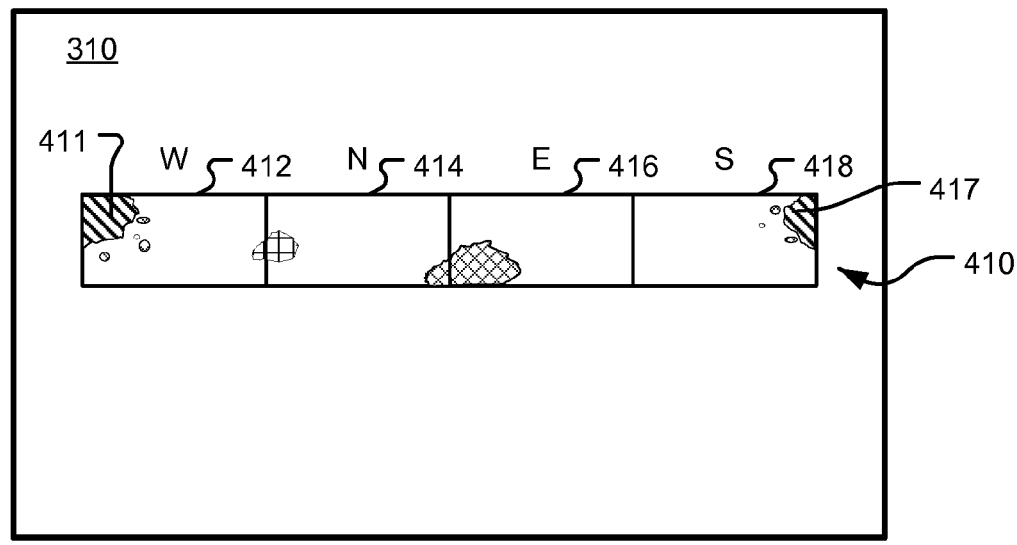
FIGS. 4A-F shows various arrangements of display window for component images from a panoramic camera system using a reflective element having 4 sides.

To display a panoramic image in the display window 310, one straight forward way is to display the panoramic image as a single image. For example, a panoramic image captured from a panoramic camera system having a 4-sided reflective element can be shown as a single image 410 in FIG. 4A. The structure of the 4-sided reflective element will result in a border line between 2 neighboring component images. The 4 component images are labeled as W 412, N 414, E 416 and S 418 corresponding to 4 directions of the 4 reflective sides. The panoramic image 410 shown in FIG. 4A is created by disjoining the component images corresponding to the W direction and the S direction. The resulting panoramic image 410 contains component images W, N, E and S from left to right. Note that while the component images are labeled with W, N, E and S directions, these 4 directions are relative directions and any of the 4 component images can be designated as the N-direction component image. Similarly, the panoramic image may be disjoined at any other boarder, such as the boarder between the N direction and the E direction resulting in a panoramic image containing component images E, S, W, and N from left to right. For a panoramic system using a panoramic annular lens, the image will look seamlessly providing continuous field-of-view. The 360-degree panoramic image can be disjoined at any desired location. The 4 component images in the 4-side reflective element camera could be stitched seamlessly by image processing technology and the image produced could also be disjoined at any desired location.

Figure 4B:
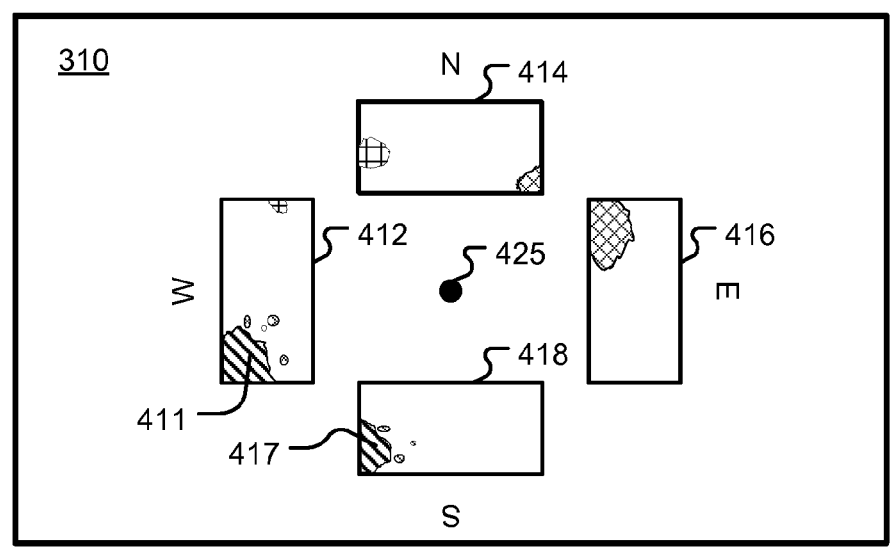

The panoramic image may also be displayed by placing component image in its respective direction. For example, the 4 component images are arranged in 4 directions with its orientation rotated to match its perspective view, as shown in FIG. 4B. The component image 414 is placed in the north position without rotation. The component image 412 is rotated 90 degrees counterclockwise and placed in the west position while the image 416 is rotated 90 degrees clockwise and placed in the east position. The component image 418 is rotated 180 degrees and placed in the south position. At the center 425 of the 4 component images represents a virtual location corresponding to the panoramic camera inside the GI track. The 4 component images represent what the panoramic camera would see in the 4 directions. Again, the W, N, E and S directions are relative directions and any component image can be designated as the N-direction component image. As mentioned earlier, the panoramic images captured by a panoramic camera system having a panoramic annular lens do not have the boarder lines. However, such panoramic image still can use the same arrangement as shown in FIG. 4B. For the arrangement of FIG. 4B, the panoramic image may be divided into 4 sub-images, rotated and placed in respective positions.

As mentioned above, a panoramic image may be very wide. An image with very wide aspect ratio (the ratio of picture width to picture height) may not result in good viewing experience. In one embodiment according to the present invention, a panoramic image may be displayed in multiple display windows. For example, each of the panoramic image with four component images (also called sub-images) may be displayed in two display windows, where two neighboring sub-images (W 412 and N 414) may be shown in first display window 420 and remaining two sub-images (E 412 and S 414) may be displayed in second display window 430. Similarly, two neighboring sub-images N 414 and E 416 may be displayed in first window 420 and remaining two sub-images S 418 and W 412 may be displayed in second display window 430. While four sub-images are illustrated as an exemplary panoramic image, the panoramic image may contain more sub-images. For example, the panoramic image may consist of six sub-images. If two display windows are used, any three consecutive sub-images may be displayed in one window and the remaining three sub-images may be displayed in another window.

Figure 4C:
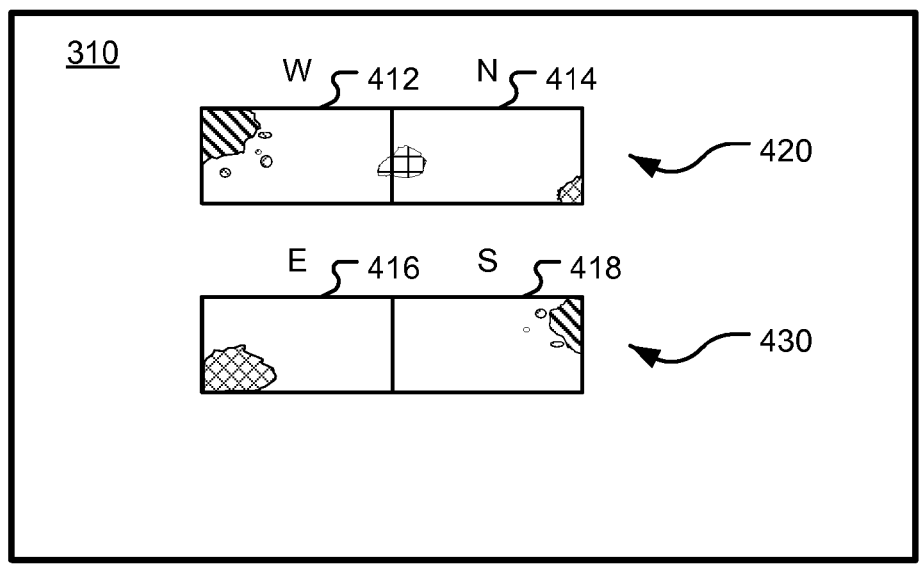

As mentioned before, the panoramic image corresponds to a 360° latitudinal FOV, the scene in the panoramic image is wrapped around the left end and the right end. The arrangement of the lens sub-system may result in a panoramic image corresponding to continuous scenes without noticeable boundaries. The formation of sub-images may be achieved by dividing the panoramic image along the latitudinal direction into sub-images. In one embodiment according to the present invention, the panoramic image is substantially equally divided into sub-images. The sub-images of the panoramic image can by cyclically shifted and still result in a proper representation of the panoramic image. While two display windows are shown in FIG. 4C, three display windows may also be used for the six sub-images, where each window consists of two neighboring sub-images. The sub-images in the three display windows correspond to three sets of cyclically shifted sub-images. While two vertically stacked display windows are shown in FIG. 4C as an example, the two display windows may be arranged side by side corresponding to the view in FIG. 4C rotated by 90°. While first window 420 and second window 430 are shown in FIG. 4C with some space apart, the two display windows may also be place next to each other without space. In yet another example according to the present invention, the panoramic image consists of four sub-images and four display windows are used. In this case, each sub-image set consist only one sub-image.

Figure 4D:
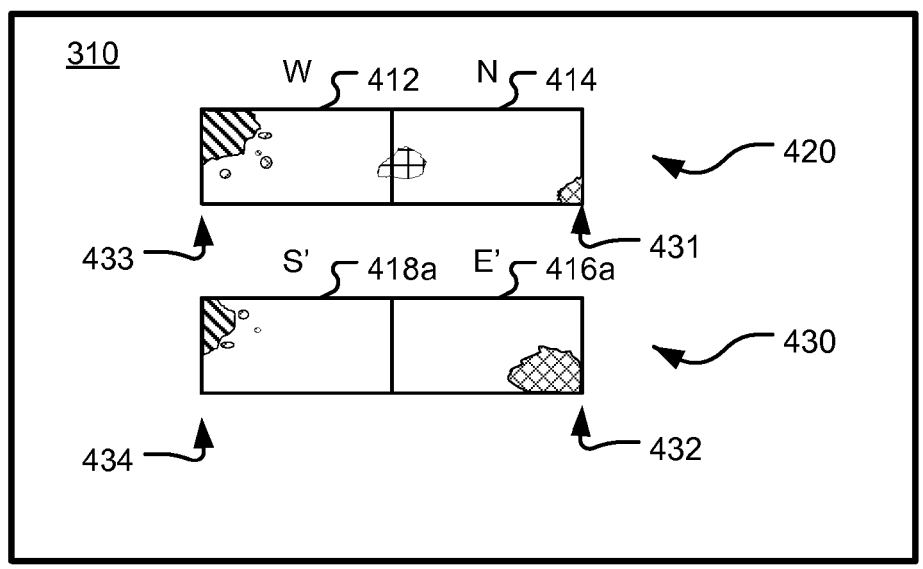
Figure 4E:
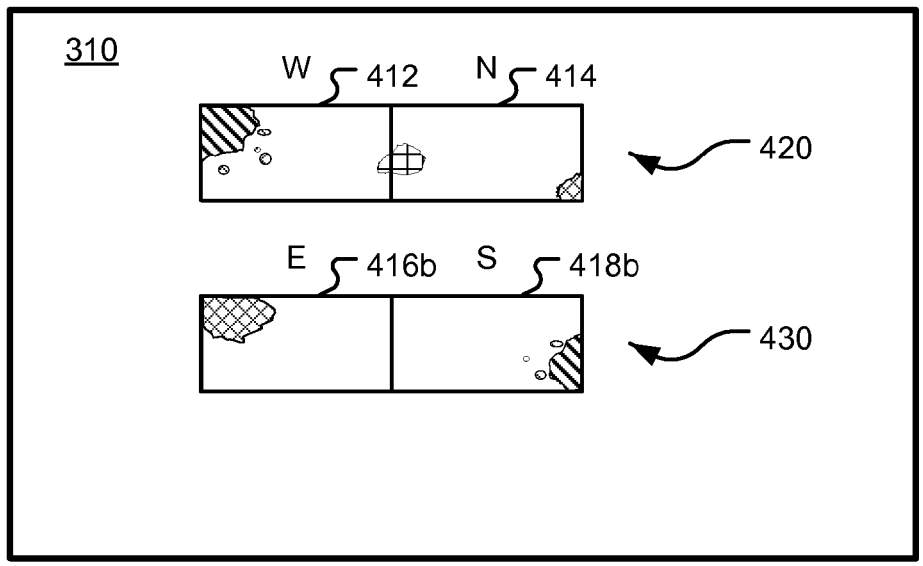
Figure 4F:
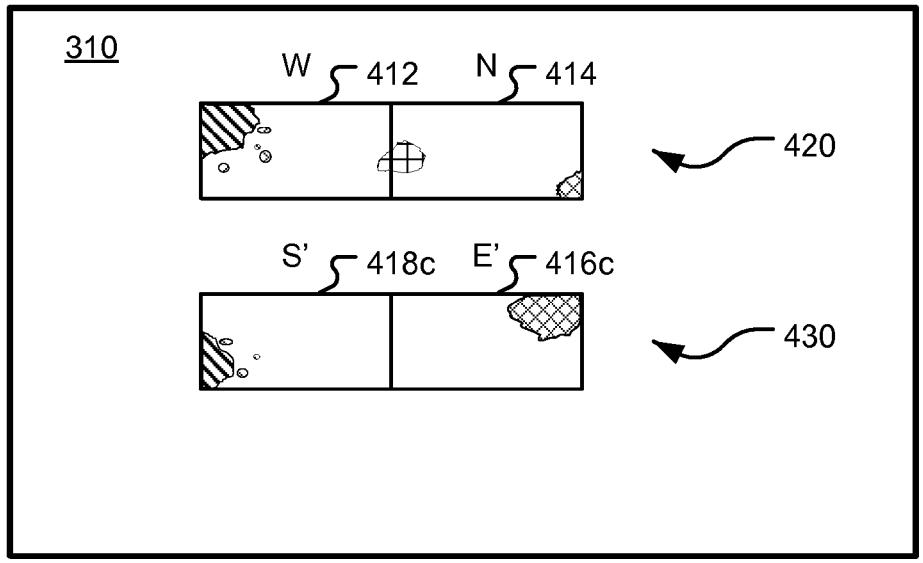

FIG. 4D illustrates another embodiment according to the present invention, where the arrangement is similar to that in FIG. 4C except that the sub-image set for second display window 430 is flipped horizontally. The flipped sub-images, S' 418*a* corresponding to S 418 and the flipped sub-images, E' 416*a* corresponding to E 416 are shown in second display window 430. When the sub-image set in the second window is flipped horizontally, right edge 431 of first display window 420 and right edge 432 of second display window 430 correspond to neighboring scenes. Similarly, left edge 433 of first display window 420 and left edge 434 of second display window 430 also correspond to neighboring scenes as well. Therefore, the arrangement shown in FIG. 4D will provide more correlated viewing experience. If more than two vertically stacked display windows are used for cyclically shifted sub-image sets, the sub-image set in every other display window will be flipped horizontally so that each display window will contain continuous scenes from an above display window on one edge and contain continuous scenes from a below display window on the other edge. In FIG. 4C and FIG. 4D, the sub-image set in second display window may be flipped vertically as shown in FIG. 4E and FIG. 4F respectively. When more than two display windows are used, the sub-image set in every other display window can be vertically flipped.

Figure 5A:
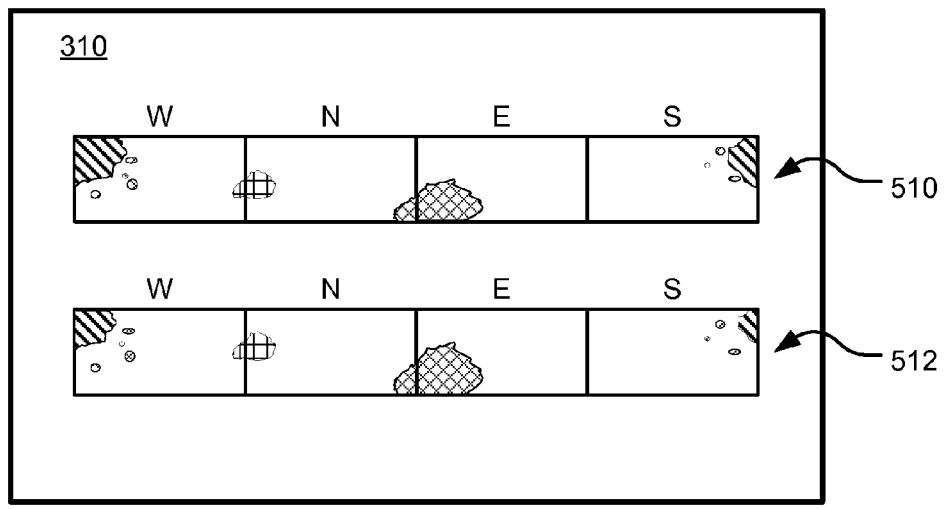
FIG. 5A shows one arrangement of display window to accommodate two video display windows simultaneously.
Figure 5B:
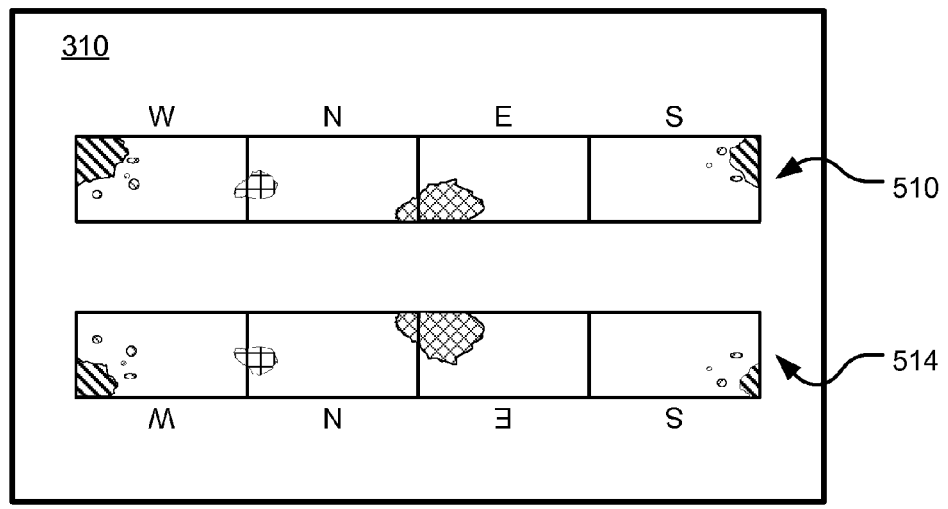
FIG. 5B shows an alternative arrangement of display window to accommodate two video display windows simultaneously.
Figure 5C:
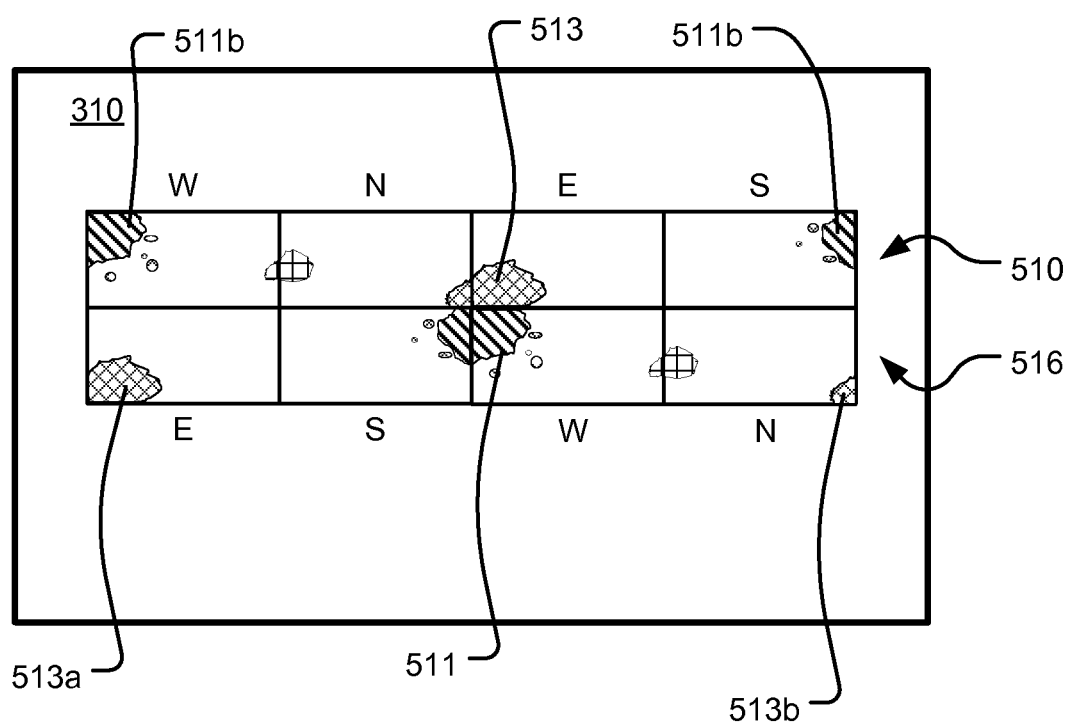
FIG. 5C shows another arrangement of display window to accommodate two video display windows showing two images of the same instance where one is a spatially shifted version of the other.
Figure 6A:
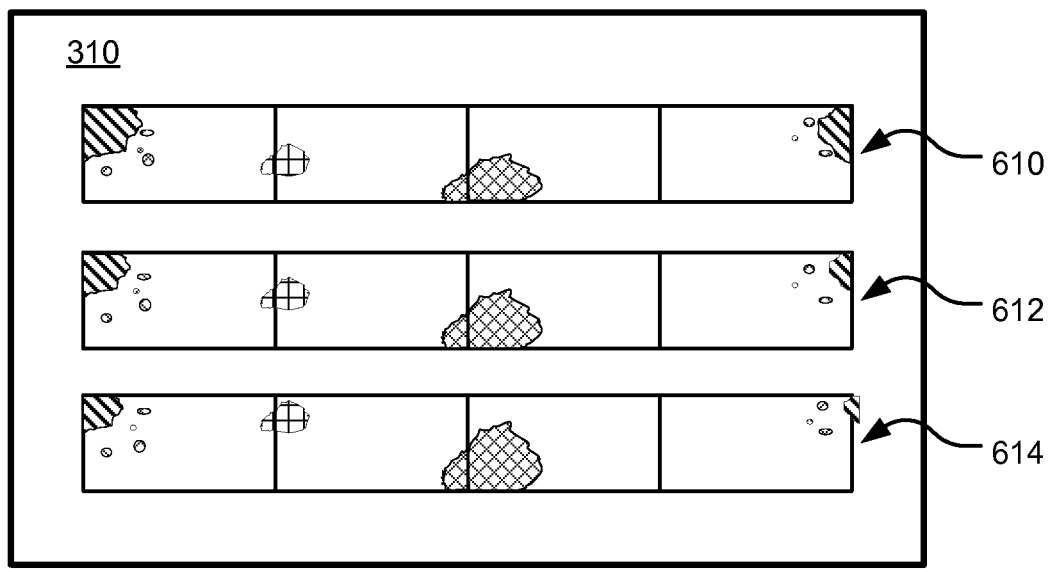
FIG. 6A shows one arrangement of display window to accommodate three video display windows simultaneously.
Figure 6B:
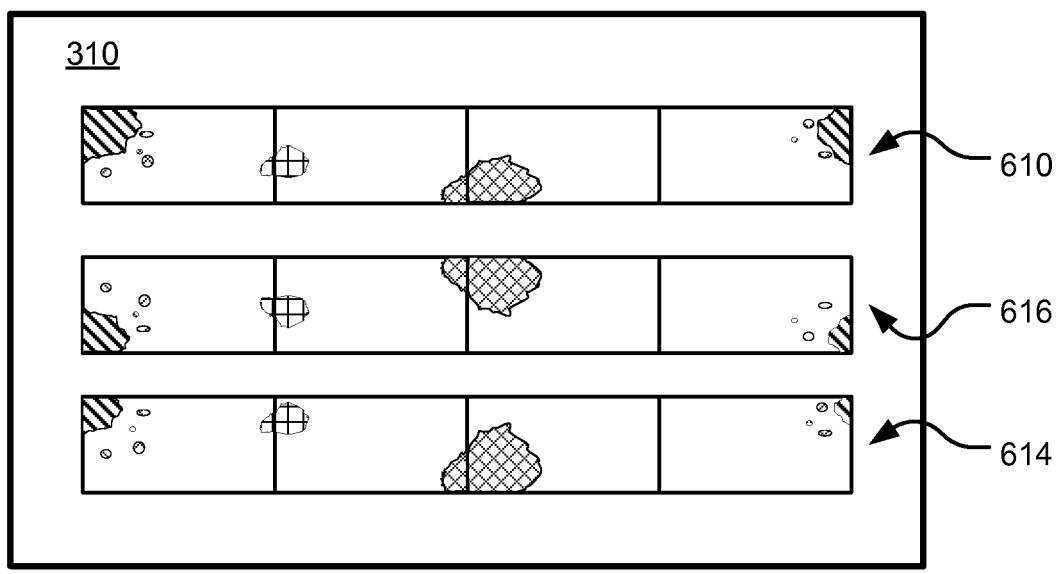
FIG. 6B shows an alternative arrangement of display window to accommodate three video display windows simultaneously.

One of the main purposes to display the sequence of capsule images is for diagnostician to analyze and examine the video to spot any possible anomaly. The factors to take into consideration for determining display arrangement include a set up for comfortable viewing and less eye fatigue, and efficient viewing time. For both traditionally colonoscopy and capsule colon endoscopy, the fatigue factors become a major problem in efficacy. With the rampant colon cancer rate, all population above 40-50 years old are recommended for regular colon examination, but there are only limited doctors. For traditional colonoscopy the detection rate drops after 3-5 procedures because the procedure requires about 30 minutes of highly technical maneuver of colonoscope. For capsule colon endoscope each reading of 10's or 100's of images per patient could easily make doctors fatigued and lower the detection rate. The vast majority public do not comply the recommendation for regular colon check up due to the invasiveness of the procedure. The capsule colon endoscope is supposed to increase the compliance rate tremendously. Consequently, the issue of reducing fatigue is critical in order to serve the increased number of colonoscopy procedures. The other critical issue is cost. The doctor's time is expensive and is the major component among both colonoscopy procedures. If the viewing throughput rate can be increased, the total healthcare cost will be substantially reduced. Currently the waiting time for a colonoscopy examination appointment is about several weeks, or may even be several months. With the dramatic increase in compliance rate helped with the use of capsule endoscope, there may not be enough doctors to meet the increasing demand. Therefore, methods and systems to reduce the viewing time without compromising the detection rate has another important meaning. The panoramic image shown in FIG. 4A is an intuitive arrangement. However, based on actual viewing experience, the image having extremely large aspect ratio (the ratio of picture width to picture height) may often cause eye fatigue. By placing multiple panoramic images in the same display window as shown in FIG. 5 and FIG. 6, it reveals a surprisingly pleasant viewing experience. In both FIG. 5 and FIG. 6, the composed images have the same picture width while the total picture height is increased. Such arrangement effectively changes the picture aspect ratio to a lower value. The aspect ratios for FIGS. 5A-C and FIGS. 6A-B are close to that of cinema viewing. Furthermore, more images are displayed in the display window of FIGS. 5A-C and FIGS. 6A-B, which implies that a shorter viewing time is required if the video is played back at the same picture rate as before.

The single image strip with high aspect ratio will not only cause fatigue but also will slow down the video reading speed. When a viewer views the video, the natural inertia is to focus on the middle and then look at one side, and then the other side. If some parts of the video on the left end attract viewer's attention, the viewer still needs to look at the right end later. This dynamic tends to slow down the video viewing and the continuous and strenuous eyeball movement will quickly get the viewer fatigued.

In FIG. 5A, two panoramic images 510 and 512 are displayed on screen at the same time. These two panoramic images 510 and 512 are selected from a sequence of panoramic images for viewing. When images correspond to an image sequence are displayed sequentially at a certain frame rate (number of frames per second), the images render themselves as a video. The display locations of the two panoramic images actually define two video display windows. Each of the two windows 510 and 512 can be used to display a sequence of panoramic images. Methods to create a multi-sequence based on a received sequence of panoramic images will be presented later. The multi-sequence consists of multiple member sequences which are derived from the original sequence. While the two panoramic images shown in FIG. 5A have the same up-right orientation, one of the two images may be displayed upside-down, i.e., being flipped vertically as shown in FIG. 5B, where the panoramic image 514 is vertically flipped image 512. Alternatively the image 512 may stay in the same orientation and the image 510 is flipped vertically. When a capsule camera travels through the GI track, the captured images will appear to move mainly in one direction when the images are shown sequentially on a screen. The configuration of FIG. 5A contains two video windows having images in the same orientation. When the two member sequences are played back as video, the contents in the two member sequences will appear to move in the same direction. On the other hand, the contents in the two member sequences corresponding to FIG. 5B will appear to move inward or outward from the center of the two video display windows. It can be a viewer's personal preference to view the two member sequences moving in the same direction or moving inward/outward from the center.

FIG. 5C shows an alternative arrangement for displaying multi-sequence where the second member sequence consists of a shifted version of the images from the original sequence. As shown in FIG. 5C, an object happens to be located between the component images W and S. Since the panoramic image is formed by stitching, from left to right, images W, N, E and S. Therefore, the object is shown as two parts 511a and 511b at both ends of the panoramic image. This split image makes it hard for the diagnostician to perform the examination. Now, the same set of component images are displayed at the bottom of the original panoramic image by shifting the component images 2 positions to the right to form an image of the second member sequence 516, as shown in FIG. 5C. The two parts of the split image are now joined as a complete image 511 in the member sequence 516. On the other hand, an object 513 in the original sequence 510 may now become split into two parts 513a and 513b in member sequence 516 if it happens to be located between component images N and E. The above example discloses the member sequence 516 is a spatially shifted version of the original sequence 510. Consequently the images in member sequence 510 will appear in member sequence 516 in a spatially shifted fashion. In this arrangement, the member sequence 510 will have to contain all the images in the original sequence to ensure every image is displayed.

A first member sequence and a second member sequence may be derived from an original sequence using 2:1 temporal sub-sampling. Since neighboring images usually have high similarity, the above spatial shifting may be applied to the second member sequence which is a temporal subset of the original sequence. In this arrangement, the total number of images in the two member sequences is the same as that of the original sequence. Since two display windows are used and the display time will be reduced to half if the display frame rate maintains the same. In addition, such arrangement provides a convenient view experience since non-split objects are always viewable in the center of the display.

In the case that the member sequence corresponding to image 510 is the original sequence, the second member sequence corresponding to image 516 as shown in FIG. 5C will have the same number of images as the original sequence. If this multi-sequence is displayed at normal speed, it will result in the same amount of viewing time. Nevertheless, the arrangement shown in FIG. 5C still provides several advantages. First, it takes care of the split object issue. An object located between any two component images will be always shown properly in one of the member sequences. Another advantage is that a diagnostician may now focus on the left half, the right half or the center part of the aggregated video without missing any component image. For example, the 4 component images on the left half of the screen include images W, N, E and S which are a complete set of component images. The 4 component images in the middle include images N, E, S and W which again are a complete set of component images. Similarly, the 4 component images on the right half of the screen contain a full set of component images. Therefore, the diagnostician doesn't have to scan images side to side and this will make the viewing experience much more pleasant and relaxed. While the example in FIG. 5C shows a panorama image having 4 component images, the present invention is also applicable to continuous panorama images without any border within the image. The panorama image is considered continuous by wrapping around the two ends that connect the scene. Therefore, the panorama image is cyclically shifted by half of the image width to generate the second member sequence.

Depending on the layout of the display screen and the size of the panoramic image, more than two member sequences may be displayed on the screen at the same time. For example, FIG. 6A shows three panoramic images being displayed in the same display window where all three images 610, 612, and 614 have the same orientation. FIG. 6B shows a similar arrangement having three panoramic images displayed concurrently in the same display window. However, the image 616 in the middle is a vertically inverted version of image 612. Therefore, the images 610 and 616 will look like they are joined in the middle between the two images and provide the same visual sensation as the images 510 and 514 of FIG. 5B. Therefore, the image 610 and the image 616 will appear move away from each other or move in toward each other depending on the image orientation and camera movement. Similarly, the images 616 and 614 will look like they are joined in the middle between the two images and provide the same visual sensation as the images 510 and 514 of FIG. 5B. In another arrangement similar to that in FIG. 6A, the orientation of the middle image 612 remains the same and both images 610 and 614 are inverted.

The multi-sequence is derived from the original sequence. One method to generate multi-sequence is to perform spatial processing on the original sequence. For example, the arrangement in FIG. 5C illustrates an example of spatial processing by cyclically rotating the original image. According to FIG. 5C, one member sequence consisting of a cyclically shifted version of the original images is generated. The cyclically shifted member sequence contains the same amount of data as the original sequence. The cyclically shifted member sequence along with the original sequence forms multi-sequence. More cyclically shifted member sequences can be formed by cyclically shifting the original image by different amount. For example, three cyclically shifted member sequences can be generated from the original sequence by cyclically shifting by 1, 2 and 3 component images respectively. Along with the original sequence, the set contains 4 member sequences. The 4 member sequences may be displayed by stacking up one member sequence on the top of the other. The order of stacking up may be selected as individual preference. For example, the original sequence may be place on the top and the member sequences cyclically shifted by 1, 2 and 3 component images may be placed below the original sequence in order. Alternatively, the original sequence may be placed on the top; the member sequence cyclically shifted by 2 component images is placed below the original sequence, followed by the member sequence cyclically shifted by 1 component image and 3 component images. The above examples are for illustration purpose to demonstrate alternatives of spatial processing to generate member sequences for multi-sequence. Other spatial processing methods to generate member sequences are also possible. The cyclical shifting method is also applicable to images having continuous scenes without borders. The amount of cyclically shifting may be arbitrary instead of the unit of component image. In the above example, one of the four member sequences is the original sequence and the other three are spatially shifted version of the original sequence. Therefore the three spatially shifted member sequences have the same number of images as the original sequences. The resulting multi-sequence will take the same amount of viewing time if it is displayed at a regular frame rate. Alternatively, four sub-sequences may be generated by 4:1 temporal sub-sampling of the original sequence, where the temporal sub-sampling will be described in more detail later. One of the sub-sequences can be used as a member sequence directly. The other three member sequences can be derived from the other three sub-sequences by spatially, cyclically shifting the respective sub-sequences at different spatial distances. Such multi-sequence is a result of temporal processing of the original sequence followed by spatial processing.

Figure 7:
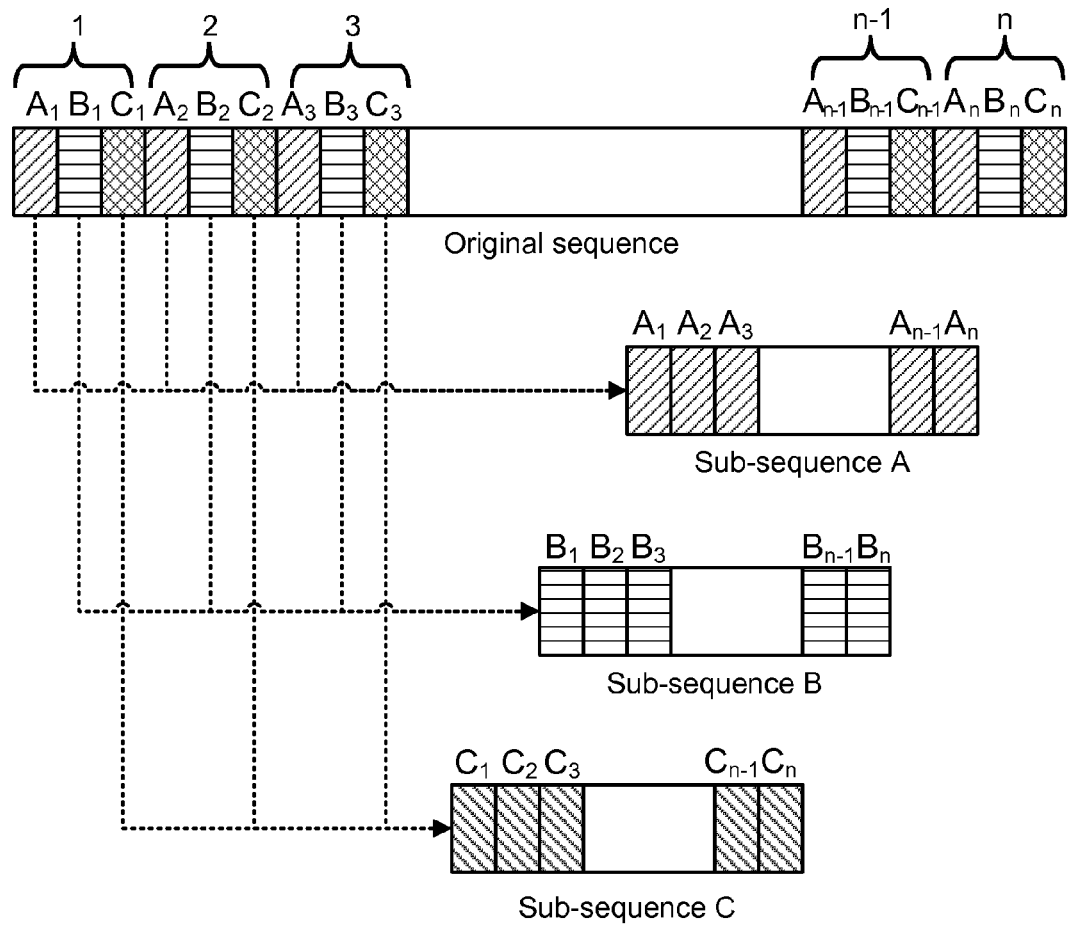
FIG. 7 shows a temporal sub-sampling method to construct member sequences from an original sequence.

Other than the spatial processing discussed above, there are also temporal methods to generate member sequences. One preferred method to temporally derive multi-sequence is shown in FIG. 7 where 3 sub-sequences are generated from the original sequence. The original sequence has a total of 3n images and each of the resulting sub-sequence contains n images. In the case that the total number of images in the original sequence is not divisible by 3, the last picture in the sequence may be repeated as needed to make the total number divisible by 3. The sub-sequence A contains images $A_1, A_2, \ldots, A_i, \ldots, A_n$, where i is the index corresponding to the temporal order that the image is displayed. Similarly, sub-sequences B and C contain images $B_i$ and $C_i$ respectively having index i corresponding to the temporal order that the images are displayed. The sub-sequences A, B and C may be used as member sequences directly. Therefore, at each time instance, respective images $A_i$, $B_i$ and $C_i$ are displayed on the screen simultaneously. It is preferred that the images displayed on the screen simultaneously have the maximum similarities among them so that it is easier for the eyes to visualize and perceive the contents. Consequently, the set of respective images $A_i$, $B_i$ and $C_i$ are chosen from consecutive images of the original sequence as shown in FIG. 7. This method of constructing the sub-sequence is often called temporal sub-sampling if the image sequence is treated as a sequence along the time domain. While the example in FIG. 7 illustrates the case having 3 member sequences, it is understood that dividing the original sequence into 3 member sequences is not a limitation of the present invention. The original sequence may be divided into any integer number of member sequences for display concurrently on the screen. If the sequence is divided into N member sequences and the total number of images in the original sequence is not divisible by N, the last image of the original sequence may be repeated as needed to make it divisible by N. While the sub-sequences may be used as member sequences directly, further spatial processing by cyclically shifting the sub-sequences at different spatial distances may be used to generate the member sequences.

Figure 8:
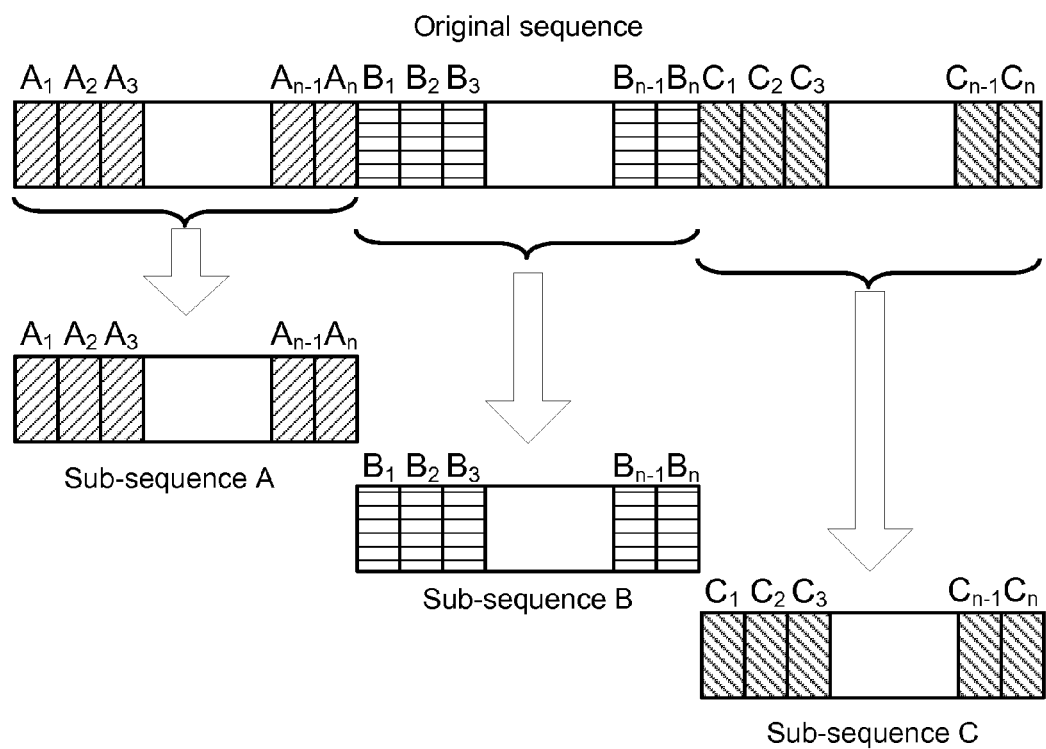
FIG. 8 shows a method of constructing member sequences from an original sequence by equally dividing the original sequence into sections.

While FIG. 7 shows temporal sub-sapling as the method for constructing multi-sequences, other methods can also be used. For example, the original sequence may be equally divided into 3 sections and the first section is assigned to the member sequence A, the second section to the member sequence B and the third section to the member sequence C as shown in FIG. 8. One advantage of this method is that, often at certain instances, the capsule camera may stay relatively stationary in some sections while the capsule camera may travel normally at other sections. Therefore, there will be some instances that images in some video windows show no motion or very little motion so that a diagnostician may focus his/her attention on images in other video windows. While the example in FIG. 8 illustrates the case that the original sequence is equally divided into 3 sections, the present invention can also be applied to cases that the original sequence is divided into other integer number of sections.

Figure 9:
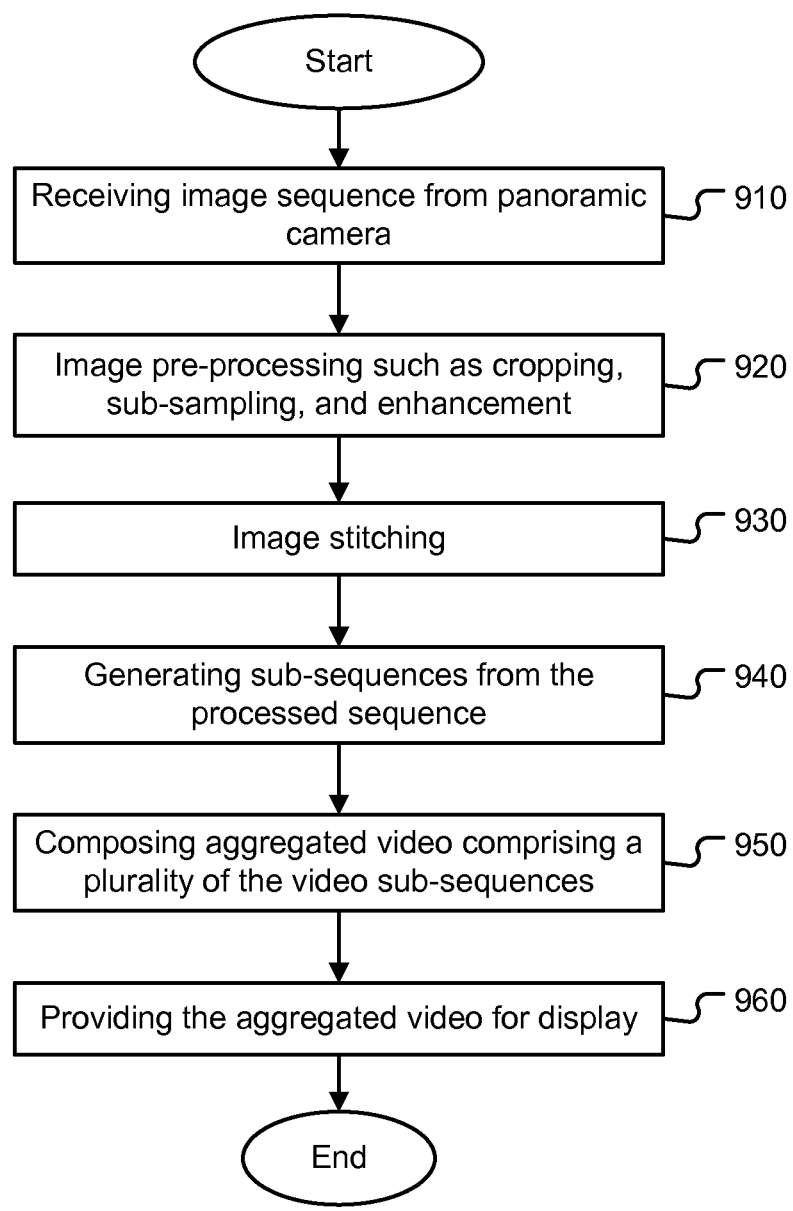
FIG. 9 shows a flowchart for system embodying the present invention.

FIG. 9 shows a flowchart for a system embodying the present invention. At step 910, an image sequence from a panoramic camera is received. Image pre-processing such as cropping, sub-sampling and enhancement is performed at step 920. The component images from all sides of the reflective element are stitched together to form a panoramic image at step 930. For some systems such as the system using a panoramic annular lens, the image captured is in a continuous field of view and there is no need for stitching. Therefore the step of stitching may be skipped for such systems. The collection of images forms an image sequence and the sequence is divided into N member sequences according a method in step 940. The member sequences are then composed into an aggregated video in step 950 and the aggregated video is displayed in step 960. The stitching for image with component images is optional. For member sequence method similar to that described in FIG. 7 the sub-sequencing could be done in real time without receiving all the images completely.

Although in this detailed description the camera cover 360 degree, but the invention could be applied to optical system cover substantially panoramically with an image or composite image with a long edge and a substantially shorter edge.

The invention may be embodied in other specific forms without departing from its spirit or essential characteristics. The described examples are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for displaying a sequence of panorama images from a capsule camera system, the method comprising:
   accepting a panorama image captured with the capsule camera system;
   generating multiple sub-image sets using a sub-image set window on the panoramic image by cyclically shifting the panoramic image; and
   displaying said multiple sub-image sets in multiple display windows, wherein each of said multiple display windows is used to display one of said multiple sub-image sets.

2. The method of claim 1, wherein the sub-image set in every other display window is flipped horizontally, vertically or both horizontally and vertically.

3. A method for displaying a sequence of panorama images from a capsule camera system, the method comprising:
   accepting a panorama image captured with the capsule camera system, wherein the panorama image consists of multiple sub-images corresponding to scenes around latitudinal field of view;
   generating multiple sub-image sets by cyclically shifting the panoramic image; and
   displaying said multiple sub-image sets in multiple display windows, wherein each of said multiple display windows is used to display one of said multiple sub-image sets.

4. The method of claim 3, wherein the sub-image set in every other display window is flipped horizontally, vertically or both horizontally and vertically.

5. A system for displaying a sequence of panorama images from a capsule camera system, the system comprising:
   an interface to accept a panorama image captured with the capsule camera system, wherein the panorama image consists of multiple sub-images corresponding to scenes around latitudinal field of view;
   means for generating multiple sub-image sets by cyclically shifting the panoramic image; and
   means for displaying said multiple sub-image sets in multiple display windows, wherein each of said multiple display windows is used to display one of said multiple sub-image sets.

6. The system of claim 5, wherein the sub-image set in every other display window is flipped horizontally, vertically or both horizontally and vertically.

7. A system for displaying a sequence of panorama images from a capsule camera system, the system comprising:
   an interface to accept a panorama image captured with the capsule camera system, wherein the panorama image consists of multiple sub-images corresponding to scenes around latitudinal field of view;
   means for generating multiple sub-image sets by cyclically shifting the panoramic image; and
   means for displaying said multiple sub-image sets in multiple display windows, wherein each of said multiple display windows is used to display one of said multiple sub-image sets.

8. The system of claim 7, wherein the sub-image set in every other display window is flipped horizontally, vertically or both horizontally and vertically.

* * * * *